US010168325B2

United States Patent
Takagi et al.

(10) Patent No.: US 10,168,325 B2
(45) Date of Patent: Jan. 1, 2019

(54) NON-SPECIFIC REACTION INHIBITOR

(71) Applicant: LSI MEDIENCE CORPORATION, Tokyo (JP)

(72) Inventors: Yoshikazu Takagi, Tokyo (JP); Yuichi Shintani, Tokyo (JP)

(73) Assignee: LSI MEDIENCE CORPORATION, Tokyo (JP)

( * ) Notice: Subject to any disclaimer, the term of this patent is extended or adjusted under 35 U.S.C. 154(b) by 346 days.

(21) Appl. No.: 14/526,415

(22) Filed: Oct. 28, 2014

(65) Prior Publication Data

US 2015/0050666 A1    Feb. 19, 2015

Related U.S. Application Data

(63) Continuation of application No. 12/674,410, filed as application No. PCT/JP2008/065032 on Aug. 22, 2008.

(30) Foreign Application Priority Data

Aug. 23, 2007    (JP) ................................. 2007-216750

(51) Int. Cl.
     *G01N 33/543*      (2006.01)
     *G01N 33/53*      (2006.01)

(52) U.S. Cl.
     CPC ... *G01N 33/54393* (2013.01); *G01N 33/5306* (2013.01)

(58) Field of Classification Search
     CPC .................... G01N 33/5306; G01N 33/54393
     See application file for complete search history.

(56) References Cited

U.S. PATENT DOCUMENTS

| | | | |
|---|---|---|---|
| 4,914,040 A * | 4/1990 | Lenz | G01N 33/5306 436/175 |
| 5,541,297 A | 7/1996 | Hansen et al. | |
| 5,804,391 A | 9/1998 | Klemt et al. | |
| 5,965,378 A | 10/1999 | Schlieper et al. | |
| 6,632,682 B1 | 10/2003 | Ziegelmaier | |
| 2002/0052009 A1 | 5/2002 | Hornauer et al. | |
| 2005/0215767 A1 | 9/2005 | Koenig et al. | |
| 2006/0246524 A1 | 11/2006 | Bauer et al. | |

FOREIGN PATENT DOCUMENTS

| | | |
|---|---|---|
| EP | 0 083 869 A1 | 7/1983 |
| EP | 0 267 690 A1 | 10/1986 |
| EP | 0 227 173 B1 | 7/1987 |
| EP | 0 292 810 A2 | 5/1988 |
| EP | 1 207 393 A1 | 5/2002 |
| JP | 11-287801 A | 10/1999 |
| JP | 2000-180446 A | 6/2000 |
| JP | 2004-325414 A | 11/2004 |
| JP | 3602135 B2 | 12/2004 |
| JP | 2006-038823 A | 2/2006 |
| WO | 93/04173 A1 | 3/1993 |
| WO | 02/064634 A2 | 8/2002 |
| WO | 2004/013287 A2 | 2/2004 |
| WO | 2004/016750 A2 | 2/2004 |

OTHER PUBLICATIONS

Shirai et al., "Treatment with Dextran-Conjugated Anti-IgD Delays the Development of Autoimmunity in MRL-lpr/lpr Mice," The Journal of Immunology, 1994, vol. 153(4), pp. 1889-1894.
Abliance, Catalog pages for "Peroxydase labeled Affinity purified anti-human antibodies," 2014, retrieved online from <http:www.abliance.com/en/Peroxydase-labeled-Affinity-purified-anti-human-secondary-antibodies> on Jun. 26, 2014.
Chan et al., "Therapeutic antibodies for autoimmunity and inflammation," Nature Reviews Immunology, 10:301-316, 2010.
Chapman, "PEGylated antibodies and antibody fragments for improved therapy: a review," Advanced Drug Delivery Reviews, 54(4):531-545, 2002.
Delgado, et al., "Enhanced tumour specificity of an anti-carcinoembrionic antigen Fab' fragment by poly(ethylene glycol) (PEG) modification," Br. J. Cancer, 73(2):175-82, 1996.
Extended European Search Report for the European counterpart of PCT/JP2008/065032 dated Oct. 6, 2010.
MBL Life Science Medical & Biological Laboratories Co., Ltd, Catalog pages for "Anti-IgM (μchain) (Human)pAb-HRP," 2014, retrieved online from <http:www.ruo.mbl.co.jp/e/dtl/A/212/> on Jun. 26, 2014.
Molecular Probes, "Nanogold® and FluoroNanogold Congugates$^{TM}$," published Mar. 29, 2002.
Stone et al., "Clinical value of ELISA assays for IgM and IgG rheumatoid factors," J. Clin. Pathol., 40(1):107-111, 1987.
Torfason et al., "False RIA IgM titres to herpes simplex virus and cytomegalovirus: factors causing them, and their absorption by protein A-sepharose/IgG-protein A-sepharose," Journal of Medical Virology, 10:157-170, 1982.

* cited by examiner

*Primary Examiner* — Galina Yakovleva

(74) *Attorney, Agent, or Firm* — Kilpatrick Townsend & Stockton LLP

(57) ABSTRACT

Disclosed is a non-specific reaction inhibitor for use in an immunological measurement, comprising a complex of an antibody or a fragment of the antibody capable of specifically binding to a non-specific reaction factor, and a polymer. The non-specific reaction inhibitor can inhibit a non-specific reaction which may interfere with the accurate detection or quantification of a trace substance in an immunological measurement method.

8 Claims, 3 Drawing Sheets

NON-SPECIFIC REACTION INHIBITOR

CROSS-REFERENCE TO RELATED APPLICATIONS

This application is a continuation of U.S. application Ser. No. 12/674,410, filed Feb. 19, 2010, which is a national phase application under 35 U.S.C. 371 of PCT/JP2008/065032, filed Aug. 22, 2008, which claims priority to Japanese Application No. 2007-216750, filed Aug. 8, 2007, the teaching of which is incorporated by reference in its entirety for all purposes.

TECHNICAL FIELD

The present invention relates to a non-specific reaction inhibitor capable of inhibiting a non-specific reaction which may interfere with the accurate detection or quantification of a trace substance in an immunological measurement method.

BACKGROUND ART

Even in a highly specific immunological measurement method utilizing an antigen-antibody reaction, there has been a problem that some samples which do not contain an antigen to be measured show positive measured values, i.e., measured values different from the true values. This phenomenon is called a non-specific reaction.

As an immunological measurement method utilizing an insoluble carrier on which an antibody specifically binding with an antigen to be measured is immobilized, a latex agglutination optical measurement method and an enzyme immunoassay are known. When such a method is used to measure the concentration of an antigen contained in samples, there are some cases where certain samples contain a factor which is different from the antigen, but can recognize and react with the immobilized antibody (a non-specific reaction factor). In these cases, such samples to be measured show positive measured values, i.e., measured values different from the true values.

The non-specific reaction factor contained in samples is not particularly limited, so long as it is a substance which is different from an antigen to be measured, and can react with an antibody-immobilized carrier. Examples of the non-specific reaction factor which frequently occurs include naturally occurring antibodies such as IgM, IgG, and IgA. When a sample is a human body fluid, such as a serum or plasma, human IgM or human IgG frequently participates in non-specific reactions, and a non-specific agglutination of latex carriers occurs in the latex agglutination optical measurement method.

As a method of inhibiting a non-specific reaction caused by the non-specific reaction factor, a method of avoiding the effect of human IgM or human IgG by supplementing a measurement reagent with an anti-human-IgM antibody, an anti-human-IgG antibody, or the like. As a concrete inhibitor added in this method, a serum component obtained from animals other than humans is proposed (patent reference 1). Patent reference 2 discloses a method of supplementing a measurement reagent with an antibody obtained by immunizing an animal with a non-specific reaction factor. A non-specific reaction can be decreased by supplementing a measurement reagent with this type of antibody.

However, IgG or IgM obtained from an animal serum has multiple sites for the recognition of an antigen. For example, a molecule of IgG has two antigen recognition sites, and a molecule of IgM has at least ten antigen recognition sites. In addition, IgG and IgM exhibit a highly hydrophobic property, in comparison with other proteins. For these reasons, when IgG or IgM coexists in the same reaction liquid with an antigen which is a target of IgG or IgM, an immunological nephelometric reaction occurs. The immunological nephelometric reaction is a phenomenon that multiple antigens are crosslinked with IgG or IgM to form a huge immunological complex, which causes cloudiness capable of being optically detected as turbidity. For example, when human IgM is added to a reaction liquid containing an antibody specific to human IgM, an immunological nephelometric reaction occurs and the reaction liquid becomes cloudy. Under these conditions, when a latex agglutination optical measurement method in which the amount of an antigen is determined by optically measuring turbidity is carried out, sometimes an accurate measured value cannot be obtained due to the immunological nephelometric reaction. As described above, a non-specific reaction due to a non-specific reaction factor can be avoided, but there remains a problem that the avoidance newly results in a secondary immunological nephelometric reaction. In addition, there is another problem that when a sample contains rheumatoid factors, the immunological nephelometric reaction is increased because the rheumatoid factors bind with the Fc region of an IgG or IgM molecule.

These problems can be solved by adding a decreased amount of antibody to a measurement reagent. However, when the amount added is less than the amount sufficient to inhibit the effect of a non-specific reaction factor, the effect of inhibiting the non-specific reaction is insufficient.

Under these circumstances, the present inventors examined a method utilizing, as a non-specific reaction inhibitor, an "antibody fragment" obtained by digesting an "antibody", for example, $F(ab')_2$ obtained by digesting an IgG molecule with a protease, pepsin. An IgG or IgM molecule contains an Fc region having a high hydrophobicity, but $F(ab')_2$ does not contain the Fc region. Therefore, when $F(ab')_2$ is used, the immunological nephelometric reaction caused by the addition of an antibody does not easily occur, and therefore, a large amount of $F(ab')_2$ can be added to a measurement reagent. In addition, the effect of rheumatoid factors can be avoided because $F(ab')_2$ does not contain the Fc region. Therefore, the above problems caused by the addition of IgG (i.e., the immunological nephelometric reaction and the effect of rheumatoid factors) can be avoided by utilizing $F(ab')_2$. Under these circumstances, the effect of $F(ab')_2$ of inhibiting a non-specific reaction was the same as that of IgG. As described above, the method utilizing an antibody fragment $F(ab')_2$ as a non-specific reaction inhibitor is more practical than the invention utilizing an antibody. The present inventors further evaluated a measurement reagent containing the $F(ab')_2$ as the inhibitor, it was found that the measurement reagent has a disadvantage in maintaining the effect of inhibiting a non-specific reaction.

The $F(ab')_2$ molecule is a molecule in which two molecules of Fab' are linked via a disulfide bond of the hinge region. $F(ab')_2$ is characterized by a high sensitivity to an oxidation-reduction reaction. $F(ab')_2$ is easily reduced and degraded into two molecules of Fab'. Further, because a serum component contains a protease which cleaves a peptide bond at the hinge region of $F(ab')_2$, $F(ab')_2$ is degraded if the purification of $F(ab')_2$ from a serum is insufficient or if the measurement reagent is contaminated with the protease or the like. Therefore, when a measurement reagent coexists with $F(ab')_2$, $F(ab')_2$ is easily degraded in accordance with a method of storing the measurement reagent. Because Fab' exhibits a very weak effect of inhibiting a non-specific reaction in comparison with an antibody or F(ab')$_2$, it was considered that the degradation of F(ab')$_2$ in the measurement reagent reduced the maintenance of the effect of inhibiting a non-specific reaction. Actually, the effect of inhibiting a non-specific reaction was not significantly observed in a measurement reagent supplemented with Fab' as a non-specific reaction inhibitor.

As prior art different from the above-mentioned inhibition of a non-specific reaction in an immunological measurement, a use of chemically-modified Fab' for an antitumor drug is known. For example, Delgado C. et al. (non-patent reference 1) disclose an antitumor drug containing Fab' chemically modified with polyethylene glycol. Patent reference 3 discloses an antitumor drug containing Fab' linked with a drug and a polymer via thiol groups of Fab'.

[patent reference 1] Japanese Unexamined Patent Publication (Kokai) No. 2006-38823
[patent reference 2] Japanese Unexamined Patent Publication (Kokai) No. 11-287801
[patent reference 3] U.S. Pat. No. 5,541,297
[non-patent reference 1] British Journal of Cancer, (United Kingdom), 1996, vol. 73, no. 2, p. 175-182

DISCLOSURE OF THE INVENTION

Problems to be Solved by the Invention

As described above, the addition of an antibody as a non-specific reaction inhibitor resulted in the immunological nephelometric reaction. The addition of F(ab')$_2$ had a disadvantage in maintaining the effect of inhibiting a non-specific reaction. Under these circumstances, an object of the present invention is to solve these problems and to provide a non-specific reaction inhibitor which is effective in small quantities, from the viewpoint of economic efficiency Means for Solving the Problems Although IgG or F(ab')$_2$ has the effect of inhibiting a non-specific reaction, Fab' has a very weak effect of inhibiting a non-specific reaction. It was suggested as the cause
(1) that Fab' has one antigen recognition site; and
(2) that Fab' can bind with an antigen, but does not have the effect of inhibiting a non-specific reaction, that is to say, there is a possibility that Fab' having a molecular size less than a certain molecular size can bind with a non-specific reaction factor, but does not inhibit the non-specific reaction caused by the non-specific reaction factor. The present inventors prepared a huge complex by linking Fab' with various polymers, and examined whether or not the effect of inhibiting a non-specific reaction was recovered. As a result, the effect of inhibiting a non-specific reaction was recovered by modifying Fab' with any one of polyethylene glycol, dextran, bovine serum albumin (BSA), and polyglutamic acid, independently from linkage types used in the modification with a polymer. This result clarified that the reason that Fab' lost the effect of inhibiting a non-specific reaction was mainly assumption (2). In particular, it was found that Fab' linked with polyethylene glycol exhibited the effect of inhibiting a non-specific reaction at a small amount (approximately ⅕ to 1/10) in comparison with IgG or F(ab')$_2$. In addition, it was found that modified Fab' did not easily cause the immunological nephelometric reaction.

A modification of a protein with polyethylene glycol has been conventionally carried out. Almost all modifications were carried out to improve the stability of a protein. When a protein was administered to a human or other animals as a therapeutic agent, the protein was often modified with a polymer to avoid the effect of a protease in a body or to lengthen the half-life in blood. By contrast, the modification of an antibody with a polymer in the present invention is carried out to increase the molecular size of a non-specific reaction inhibitor containing the antibody fragment, and thus, the object of the present invention is different from that of known polymer-modified products, i.e., the improvement of stability.

A chemical modification of a protein with a polymer is a known method. A review by Roberts M. J. et al. (Advanced Drug Delivery Reviews 2002, 54, 459-476) and a review by Francesco M. et al. (Biomaterials 2001, 22, 405-417) disclose major methods of the chemical modification. For example, a method of linking a polymer to a protein by utilizing, as a target, an amino group of the side chain of amino acids which constitute the protein, a thiol group of a cysteine residue, a carboxyl group of the carboxyl terminus, an amino group of the amino terminus, or a hydroxyl group of a serine residue, a threonine residue, or the like, is disclosed. Further, a method of linking a polymer to an antibody or an antibody fragment is a known method. In particular, when an antibody is chemically modified, it is considered useful that a chemically modified antibody is prepared without the loss of an antibody activity, i.e., an activity of binding with an antigen. As disclosed in a review by Andrew P. et al. (Advanced Drug Delivery Reviews, 2002, 54, 531-545), because the antigen recognition site contains amino groups or carboxyl groups, when a polymer is linked by utilizing these functional groups as a target, the antigen recognition site is often masked with the polymer, and as a result, the antibody activity is decreased by the chemical modification. To avoid the disadvantage associated with such a polymer modification, for example, a method of linking a polymer by utilizing as a target a thiol group of the hinge region of Fab' or a thiol group of reduced IgG is known. A review by Slinkin M. A. et al. (Bioconjug Chem. 1992, 3(6), 477-483) discloses a working example in which a polymer was linked to a thiol group of an antibody fragment Fab'. A review by Delgado C. et al. (Br J. Cancer. 1996, 73(2), 175-182) discloses a working example of an antitumor drug containing Fab' chemically modified with polyethylene glycol. U.S. Pat. No. 5,541,297 discloses an antitumor drug containing Fab' linked with a drug and a polymer via thiol groups of Fab'.

Diagnosis and treatment can be generally classified into an in vivo case and an in vitro case. Almost all uses of a polymer-modified antibody are utilized in the treatment or diagnosis in vivo. For example, when an antibody linked to a drug or an isotope is administered into a body as a therapeutic agent or a detecting agent for a lesion such as a tumor, the antibody is modified with a polymer. By contrast, in the diagnosis in vitro, no use of a polymer-modified antibody has been found, and no polymer-modified antibody has been utilized. An agent is not administered into a body in vitro, in contrast with in vivo cases. Therefore, when the use in vitro was examined, remarkably advantageous effects other than improvement of stability were necessary. As described above, the present invention provides a new application in the diagnosis in vitro by newly finding usefulness as a "non-specific reaction inhibitor".

The present invention is to provide a new use as a "non-specific reaction inhibitor", and the present invention shows advantageous effects in comparison with conventional techniques of inhibiting a non-specific reaction.

The present inventors conducted intensive studies on non-specific reaction inhibitors and, as a result, found that problems involving the immunological nephelometric reaction and the maintenance of storage could be solved by chemically linking a polymer to an antibody specific to a non-specific reaction factor or a fragment of the antibody, and that the polymer-modified product exhibited the effect of inhibiting a non-specific reaction when small quantities were used.

The present invention relates to a non-specific reaction inhibitor for use in an immunological measurement, comprising a complex of an antibody or a fragment of the antibody capable of specifically binding to a non-specific reaction factor, and a polymer.

According to a preferred embodiment of the non-specific reaction inhibitor of the present invention, the polymer is a compound selected from the group consisting of a polysaccharide, a protein, and an organic high molecular weight polymer, and is more preferably polyethylene glycol.

According to another preferred embodiment of the non-specific reaction inhibitor of the present invention, the molecular weight of the polymer is 200 Da to 1000 kDa.

According to still another preferred embodiment of the non-specific reaction inhibitor of the present invention, the fragment of the antibody is F(ab')$_2$, Fab', Fab, Fd, an L chain, an H chain, or reduced IgG (rIgG).

According to still another preferred embodiment of the non-specific reaction inhibitor of the present invention, the bonding of the antibody or a fragment thereof to the Polymer is a chemical modification utilizing a thiol, amino, hydroxyl, or carboxyl group, or a biotin-avidin binding.

Further, the present invention relates to an immunological measurement method, characterized by using a complex of an antibody or a fragment of the antibody capable of specifically binding to a non-specific reaction factor, and a polymer.

According to a preferred embodiment of the immunological measurement method of the present invention, the method is a latex agglutination optical measurement method, an enzyme immunoassay, a nephelometric immunoassay, an enzyme-linked immunosorbent assay, a fluoroimmunoassay, or a radioimmunoassay.

Effects of the Invention

According to the present invention, the effect of inhibiting a non-specific reaction is remarkably increased by linking a polymer to an antibody against a non-specific reaction factor, or a fragment of the antibody, and a non-specific reaction can be inhibited with a small quantity (approximately ⅕ to ¹/₁₀) compared to a conventional antibody without such a modification. According to the present invention, problems caused by the addition of an antibody, i.e., the problem about the generation of the immunological nephelometric reaction and the problem about the maintenance, can be solved.

BEST MODE FOR CARRYING OUT THE INVENTION

Figure 1:
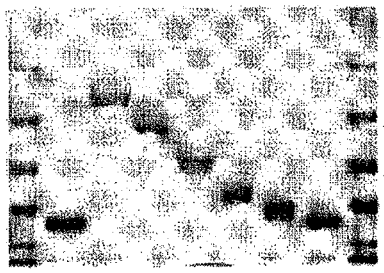
FIG. 1 shows the result of SDS-polyacrylamide gel electrophoresis (SDS-PAGE) of Fab'Mals and thiol-group-blocked Fab' prepared in Example 1.

The non-specific reaction inhibitor of the present invention comprises a complex (hereinafter referred to as the polymer-modified antibody) of an antibody (anti-non-specific-reaction-factor antibody) or a fragment of the antibody capable of specifically binding to a non-specific reaction factor, and a polymer.

The term "non-specific reaction factor" as used herein means a substance which causes a non-specific reaction in an immunological measurement method utilizing an antigen-antibody reaction. More particularly, examples of the factor when a human body fluid is used as a sample include human IgM, human IgG, human IgA, human IgE, human IgD, and factors capable of binding to these human Igs (for example, complement, rheumatoid factors, Fc receptor, and the like). Examples when a body fluid derived from animals other than humans is used as a sample include IgM, IgG, IgA, and IgE of the animal, and factors capable of binding to these Igs. An antibody specific to a non-specific reaction factor is, when the non-specific reaction factor is an IgM-type non-specific reaction factor, an anti-human-IgM antibody (i.e., an antibody against human IgM). When the factor is an IgA-type non-specific reaction factor, the antibody specific to a non-specific reaction factor is an anti-human-IgA antibody. When the non-specific reaction inhibitor of the present invention is added to an immunological measurement reagent, and it is considered that multiple non-specific reaction factors cause non-specific reactions (for example, IgM, IgG, and IgA are non-specific reaction factors), it is preferable that an embodiment of the non-specific reaction inhibitor of the present invention prepared using an anti-IgM antibody, an anti-IgG antibody, and an anti-IgA antibody is added to the measurement reagent. The present invention is not limited to embodiments in which the non-specific reaction inhibitor contains only one component as the anti-non-specific-reaction-factor antibody.

Examples of the immunological measurement method include a latex agglutination optical measurement method, an enzyme immunoassay, a nephelometric immunoassay, an enzyme-linked immunosorbent assay, an fluoroimmunoassay, a radioimmunoassay, and the like. An antigen-antibody reaction is utilized in all of these methods and assays, and a polyclonal antibody or a monoclonal antibody can be used as the antibody used in detecting a target antigen.

The antibody capable of specifically binding to a non-specific reaction factor may be prepared by subjecting, for example, an antiserum or plasma obtained by immunizing an animal with the non-specific reaction factor, a normal animal serum, a monoclonal antibody specific to the non-specific reaction factor, a recombinant antibody (including a chimeric antibody) specific to the non-specific reaction factor, or the like, to a commonly-used conventional purification method. These antibodies include a polyclonal antibody or a monoclonal antibody. Examples of the class of antibodies vary according to the type of animal, but include IgG, IgM, IgA, and the like. Examples of the animal include a rabbit, a goat, a bovine, a mouse, a rat, a swine, a chicken, and the like. Examples of the purification method include salting out, electrophoresis, gel filtration, hydrophobic chromatography, affinity chromatography, and the like.

The antibody fragment is not particularly limited, so long as it is a portion of the above-mentioned antibody obtainable by treating the antibody with, for example, an enzyme, a reducing agent, or a combination thereof, and it can bind with the non-specific reaction factor. The antibody fragment may be prepared by a known method, for example, digestion with an enzyme such as papain, pepsin, or trypsin, cleavage of a disulfide bond with a reducing agent, or a combination thereof. For example, an antibody (entire antibody) is digested with papain to obtain an Fab fragment and an Fc fragment. An antibody is digested with pepsin to obtain F(ab')$_2$, and F(ab')$_2$ is reduced with a reducing agent (for example, dithiothreitol, 2-mercaptoethanol, TCEP·HCl [Tris (2-carboxyethyl)phosphine hydrochloride], 2-mercaptoethylamine, or the like) to obtain an Fab' fragment. The Fab' fragment is treated with an SH reagent such as iodoacetamide to obtain an L chain and Fd.

An antibody (entire antibody) is reduced with a reducing agent (for example, dithiothreitol, 2-mercaptoethanol, TCEP. HCl [Tris (2-carboxyethyl)phosphine hydrochloride], 2-mercaptoethylamine, or the like) and then, is treated with an SH reagent such as iodoacetamide to obtain an L chain and an H chain, or rIgG in which only the bonding between H chains is cleaved.

The antibody fragment used in the present invention is not particularly limited, so long as it can bind with the non-specific reaction factor. For example, F(ab')$_2$, Fab', Fab, Fd, an L chain, an H chain, and rIgG are antibody fragments having an antigen-binding activity. Antibody fragments other than F(ab')$_2$ and Fab', which are concretely described in Examples described below, for example, Fab, Fd, an L chain, an H chain, or rIgG, may be used as an active ingredient of the non-specific reaction inhibitor of the present invention by linking a polymer thereto via a thiol group, an amino group, or a carboxyl group as a target. It is preferable in the present invention that Fab' modified with a polymer is used as an active ingredient of the non-specific reaction inhibitor.

Examples of the polymer-modified antibody (i.e., a complex of an anti-non-specific-reaction-factor antibody or a fragment thereof and a polymer) used in the non-specific reaction inhibitor of the present invention include a chemically-modified antibody prepared by chemically modifying an anti-non-specific-reaction-factor antibody or a fragment thereof with a polymer, and a complex of an anti-non-specific-reaction-factor antibody or a fragment thereof and a polymer via a biotin-avidin binding.

In the chemical modification, for example, a thiol group, an amino group, a hydroxyl group, or a carboxyl group of the antibody is used as a target, and a linkage may be formed via a "reactive derivative".

Examples of a "reactive derivative" used in the modification utilizing a thiol group as a target include a compound containing a thiol-selective reactive group, for example, maleimides and vinyl sulfones. Further, a polymer to which a reactive derivative is directly linked, or a cross-linking agent containing a reactive derivative may be used.

Examples of a "reactive derivative" used in the modification utilizing an amino group as a target include N-hydroxysuccinimide (NHS) esters, N-hydroxysulfosuccinimide (Sulfo-NHS) esters and the like. Further, a compound containing an aldehyde group (such as glutaraldehyde), a polymer previously containing an aldehyde group, or the like may be used.

In the modification utilizing a carboxyl group as a target, for example, carbodiimide (1-ethyl-3-[3-dimethylaminopropyl]carbodiimidehydrochloride) may be used as a catalyst to perform a reaction with an amino group to obtain a complex.

In the modification utilizing a hydroxyl group as a target, for example, a compound containing an isocyanate derivative may be used to prepare a complex.

These polymers into which a reactive derivative is introduced may be obtained as a commercially available product (for example, NOF CORPORATION), or may be prepared by conventional chemical procedures.

The present invention includes embodiments utilizing, as a binding between the antibody and the polymer, a linkage type which is not a covalent bond but shows a high affinity, like a biotin-avidin binding.

Examples of the polymer which may be used in the present invention include polysaccharides, proteins, and organic high molecular weight polymers.

The polysaccharides include, for example, dextran, dextrin, agarose, carboxymethyl (CM) cellulose, heparin, a soluble starch, and the like. A straight-chain polysaccharide or a branched-chain polysaccharide may be used.

A modification of a protein with polysaccharides may be carried out by conventional methods, for example, periodate oxidation, a cyanogen bromide method, a carbodiimide method, a cyanuric chloride method, an epichlorohydrin method, an SPDP (N-Succinimidyl 3-[2-pyridyldithio] propionate) reagent method, an active ester method, or the like. These polysaccharides into which a reactive derivative is introduced may be obtained as a commercially available product, or may be prepared by conventional chemical procedures.

The proteins are complexes in which multiple amino acids are linked via peptide bonds. The proteins may be purified from an animal, may be artificially prepared by gene engineering, or may be prepared by chemical synthesis as synthetic peptides. Examples of the proteins include casein, milk casein, gelatin, recombinant albumin, and the like. Examples of poly(amino acids) include homopolymers of arginine, lysine, glutamic acid, or the like, and random polymers of lysine and glycine, lysine and serine, or the like. Such a protein may be linked to an antibody, for example, by linking a crosslinking agent to a target such as an amino, carboxyl, or sulfide group of the protein, and then linking the resulting product to the antibody via the crosslinking agent. Alternatively, a protein may be linked to an antibody by using carbodiimide as a catalyst. In the present invention, it is preferable to react an amino group of a protein with a crosslinking agent such as EMCS [N-(6-maleimidocaproyloxy)succinimide; dojin] or SMCC [succinimidyl 4-(N-maleimidomethyl)cyclohexane carbonate; dojin] and further react the crosslinking agent with a sulfide group of an antigen fragment. The protein into which a reactive derivative is introduced, which may be used in preparing the non-specific reaction inhibitor of the present invention, may be obtained as a commercially available product, or may be prepared by conventional chemical procedures.

Examples of the organic high molecular weight polymers include polyethylene glycol, polyvinyl alcohol, polyacrylic alcohol, polyethyleneimine, poly(methyl methacrylate), polyacrylic acid, polyallylamine, and polysaccharides. A straight-chain organic high molecular weight polymer or a branched-chain organic high molecular weight polymer, or a random copolymer consisting of multiple types of monomers may be used. A synthetic polymer having a spherical structure such as a dendrimer may be used. A synthetic polymer or a natural polymer may be used.

Polyethylene glycol is a polymer having a basic structure in which ethylene glycol is polymerized. Polyethylene glycol can be linked to an antibody by utilizing a functional group introduced into a hydroxyl group of polyethylene glycol. Activation for linking polyethylene glycol to an antibody may be carried out by using, for example, cyanuric chloride, carbodiimidazole, N-hydroxysuccinimide, or carbodiimide. A commercially available product may be used as the polyethylene glycol to which a functional group is introduced. An efficient preparation may be carried out by using commercially available polyethylene glycol to which a maleimide, succinimide, amino, or sulfide group is introduced. Polyethylene glycol to which a maleimide or succinimide group is introduced is preferable because it is a good binding efficiency to an antibody. A straight-chain polyethylene glycol or a branched-chain polyethylene glycol may be used. Polyethylene in which part thereof is replaced with another chemical structure, or polyethylene modified with another polymer or compound may be used.

A chemical modification with organic high molecular weight polymers other than polyethylene glycol may be carried out by linking them to an antibody via a functional group introduced into the organic high molecular weight polymer, like the chemical modification with polyethylene glycol. When an organic high molecular weight polymers containing a reactive derivative are used, the introduction of a new functional group is not necessarily needed in a preparation step. In the present invention, it is preferable to use a polymer to which a maleimide, succinimide, amino, or sulfide group is introduced. The organic high molecular weight polymers into which a reactive derivative is introduced may be obtained as a commercially available product, or may be prepared by conventional chemical procedures.

The molecular size of the organic high molecular weight polymers is not particularly limited, but the average molecular weight thereof is generally approximately 200 Da to 1000 kDa, for example, 1 kDa to 1000 kDa, preferably 10 kDa to 100 kDa. The average molecular weight of polyethylene glycol is preferably 20 kDa to 200 kDa. The molecular size may be approximately selected in accordance with the type of the polymer, in view of hydrophilicity, a three-dimensional structure, the effect of inhibiting a non-specific reaction, or the like.

The non-specific reaction inhibitor can be used by adding the polymer-modified antibody (for example, polymer-modified anti-non-specific-reaction-factor antibody or a fragment thereof) as the active ingredient to an immunological measurement system. More particularly, a solution containing a modified fragment of an antibody specific to a non-specific reaction factor is prepared; the solution is added to a sample to react the antibody with the non-specific reaction factor, before an antibody specific to an antigen to be measured is reacted with the antigen; and the non-specific reaction caused by the non-specific reaction factor may be inhibited. Alternatively, a modified fragment of an antibody specific to a non-specific reaction factor is added to a solution containing an antibody specific to an antigen to be measured; the solution is added to a sample to react the non-specific reaction factor with the antibody specific to the factor; and the non-specific reaction caused by the non-specific reaction factor may be inhibited.

Examples of an immunological measurement reagent include elastase, cystatin C, sEs (soluble E-selectin), SF (soluble fibrin), PC (protein C), PPI (plasmin-plasmin inhibitor), cTn (thrombomodulin), myoglobin, CK-MB, BNP (B-type natriuretic peptide), AFP (α-fetoprotein), β2m (β-2-microglobulin), CEA (carcinoembryonic antigen), ferritin, CA19-9 (carbohydrate antigen 19-9), PAP (prostatic acid phosphatase), PSA (prostate-specific antigen), CRP (C-reactive protein), Mb (myoglobin), RF (rheumatoid factor), ASO (antistreptolysin-O), FDP (fibrin degradation products), AT III (antithrombin III), plasminogen, α2PI (α-2-plasmin inhibitor), D-dimer (fibrin degradation products D-fragment dimer), IgG (immunoglobulin G), IgA (immunoglobulin A), IgM (immunoglobulin M), IgE (immunoglobulin E), C3 (the third component of complement), C4 (the fourth component of complement), urinary albumin, hCG (human chorionic gonadotrophin), hPL (human placental lactogen), insulin, HBs antigen (hepatitis B surface antigen), HBs antibody (anti-hepatitis B surface antigen antibody), HBc antibody (anti-hepatitis B core antigen antibody), HCV antibody (anti-hepatitis C virus antibody), *Treponema* (anti-*Treponema pallidum* antibody), TSH (thyroid stimulating hormone), LH (luteinizing hormone), FSH (follicle stimulating hormone), digoxin, digitoxin, quinidine, procainamide, NAPA (N-acetylprocainamide), theophylline, phenyloin, phenobarbital, carbamazepine, valproic acid, ethosuccimide, gentamicin, tobramycin, amikacin, vancomycin, cyclosporine A, B12 (vitamin B12), folic acid, T3 (triiodothyronine), T4 (thyroxine), and estrogen.

EXAMPLES

The present invention will now be further illustrated by, but is by no means limited to, the following Examples.

Example 1

[Object]

Anti-non-specific reaction factors such as IgG or F(ab')$_2$ show a strong effect of inhibiting a non-specific reaction, but the effect of Fab' is weak. As the cause, (1) the possibility that multiple antigen recognition sites are needed in a molecule to show the effect of inhibiting a non-specific reaction, and (2) the possibility that the molecular size of a non-specific reaction inhibitor affects the inhibitory effect are considered. This Example was carried out to examine these hypotheses. If a molecule having a single antigen recognition site (such as Fab') exhibits the effect of inhibiting a non-specific reaction, the possibility of (1) can be denied. The possibility of (2) can be tested by preparing various polymers having a different molecular size and examining the effect of inhibiting a non-specific reaction.

[Methods]

To evaluate the effect of inhibiting a non-specific reaction by polyethylene glycol modification, a fragment (Fab') of an IgG specific to a human IgM was used to prepare a polyethylene-glycol-modified Fab' (hereinafter referred to as Fab'Mal). The modification with polyethylene glycol was carried out by linking a molecule of polyethylene glycol to a molecule of Fab' via the thiol group contained in the hinge region of the Fab'. This modification form was used to avoid the linkage of polyethylene glycol to the antigen recognition site of the Fab'. A rabbit Fab' was selected, and polyethylene glycol having a maleimide group at the terminus of only one side was used as a modifier. Further, to examine the differences in the effect of inhibiting a non-specific reaction caused by the length (molecular weight) of polyethylene glycol used in modification, polyethylene glycols having a length of 2 kDa, 5 kDa, 12 kDa, 20 kDa, or 30 kDa were used as a modifier to prepare multiple Fab'Mals having various molecular weights. As a negative control, Fab' in which the thiol group was blocked with N-ethylmaleimide to avoid a reverse reaction from Fab' to $F(ab')_2$ (hereinafter referred to as thiol-group-blocked Fab') was used. With respect to the thiol-group-blocked Fab', Fab'Mal of 2 kDa, Fab'Mal of 5 kDa, Fab'Mal of 12 kDa, Fab'Mal of 20 kDa, and Fab'Mal of 30 kDa, their effects of inhibiting a non-specific reaction were evaluated.

[Preparation of Fab'Mals]

A rabbit anti-human IgM polyclonal antibody IgG (homemade) was digested with pepsin to prepare $F(ab')_2$. The resulting $F(ab')_2$ was adjusted to 5 mg/mL using a 200 mmol/L tris(hydroxymethyl)aminomethane buffer (pH 8.2) containing 150 mmol/L NaCl. $F(ab')_2$ was reduced with 10 mmol/L 2-mercaptoethylamine at 37° C. for 30 minutes, and subjected to gel filtration using a 50 mmol/L phosphate buffer (pH 6.0) containing 5 mmol/L EDTA, as a running buffer, to collect an Fab' fraction. To a 5 mg/mL Fab' solution, polyethylene glycol of 30 kDa having a maleimide group (manufactured by NOF CORPORATION) was added to carry out a reaction at 4° C. for 4 hours while stirring. The resulting reaction liquid was subjected to gel filtration to collect an Fab'Mal fraction, which was concentrated to approximately 5 mg/mL. In a similar fashion, Fab'Mals having a molecular weight of 2 kDa, 5 kDa, 12 kDa, or 20 kDa were prepared.

[Preparation of Thiol-Group-Blocked Fab']

A rabbit anti-human IgM polyclonal antibody IgG (homemade) was digested with pepsin to prepare $F(ab')_2$. The resulting $F(ab')_2$ was adjusted to 5 mg/mL using a 200 mmol/L tris(hydroxymethyl)aminomethane buffer (pH 8.2) containing 150 mmol/L NaCl. $F(ab')_2$ was reduced with 10 mmol/L 2-mercaptoethylamine at 37° C. for 30 minutes, and subjected to gel filtration using a 50 mmol/L phosphate buffer (pH 6.0) containing 5 mmol/L EDTA, as a running buffer, to collect an Fab' fraction. To a 5 mg/mL Fab' solution, 5 mmol/L N-ethylmaleimide (manufactured by Sigma-Aldrich Corporation) was added to carry out a reaction at 4° C. for 4 hours while stirring. The resulting reaction liquid was subjected to gel filtration to collect a thiol-group-blocked Fab' fraction, which was concentrated to approximately 5 mg/mL.

The result of SDS-polyacrylamide gel electrophoresis (SDS-PAGE) of the resulting Fab'Mals and thiol-group-blocked Fab' is shown in FIG. 1. In FIG. 1, markers, thiol-group-blocked Fab', 30 kDa Fab'Mal, 20 kDa Fab'Mal, 12 kDa Fab'Mal, 5 kDa Fab'Mal, 2 kDa Fab'Mal, thiol-group-blocked Fab', and markers are shown (from the left lane).

[Assay Conditions for Evaluating the Effects of Non-Specific Reaction Inhibitors]

The effects of the Fab'Mals and the thiol-group-blocked Fab' on the inhibition of a non-specific reaction were examined by a latex agglutination optical measurement method. A D-dimer was used as an antigen measured, and two types of samples (sample A and sample B) were used as samples to be assayed. These samples were human plasma samples characterized in that the non-specific reaction as described above occurs in the measurement using a reagent for measuring a D-dimer (LPIA-ACE D-dimer II; Mitsubishi Chemical Medience Corporation) and the non-specific reaction substance is an IgM. The measurement was carried out by automated procedures using an automatic analyzer HITACHI 7170 (manufactured by Hitachi High-Technologies Corporation). The measurement using HITACHI 7170 was mainly composed of two steps. In the first step, samples to be measured were diluted with a first reagent (hereinafter referred to as R1) to prepare a reaction solution. In the second step, to this reaction solution, a second reagent (hereinafter referred to as R2) characterized by containing latex particles on which an antibody specific to a D-dimer had been immobilized was added, to generate a latex agglutination reaction. This agglutination reaction was optically monitored to quantify the D-dimer or the non-specific reaction factor contained in the samples to be assayed. In this Example, each of the Fab'Mals or the thiol-group-blocked Fab' was added to R1 to absorb the non-specific reaction substance in the first step. This addition to R1 was carried out so that the concentration of each of the Fab'Mals or the thiol-group-blocked Fab' became 100 mg/L. The Fab'Mals and the thiol-group-blocked Fab' used in this Example had been subjected to affinity chromatography to remove components capable of reacting with fibrin degradation products (including the D-dimer). The sample to be measured, R1, and R2 were mixed at a ratio of 7 μL:125 μL:125 μL. The latex agglutination was detected at a wavelength of 800 nm. Measurement values were calculated from absorbances, using a calibration curve prepared by measuring the D-dimer at known concentrations.

[R2 for Measuring D-Dimer]

A latex reagent contained in an in vitro diagnostic reagent (LPIA-ACE D-dimer II; distributed by Mitsubishi Chemical Medience Corporation) was used as the R2 reagent. This product contains as a component insoluble carriers to which a monoclonal antibody specific to D-dimer is linked by a chemical bond.

[Results]

The result is shown in Table 1. As shown in Table 1, all Fab'Mals exhibited the effect of inhibiting the non-specific reaction. The effect of Fab'Mals was dependent on the molecular weight, and it was found in the modification with polyethylene glycol that polyethylene glycol having a higher molecular weight was superior in the effect of inhibiting the non-specific reaction.

TABLE 1

| Sample | SH-blk Fab' | Fab'Mal | | | | | Not added |
| --- | --- | --- | --- | --- | --- | --- | --- |
| | | 2 kD | 5 kD | 12 kD | 20 kD | 30 kD | |
| A (μg/mL) | 7.08 | 2.95 | 1.18 | 0.90 | 1.09 | 0.85 | 8.52 |
| B (μg/mL) | 20.28 | 18.13 | 7.79 | 0.26 | 0.06 | 0.04 | 17.66 |

(SH-blk Fab': thiol-group-blocked Fab')

Example 2

[Object]

The result of Example 1 revealed that Fab' having a single site for antigen recognition shows the effect of inhibiting a non-specific reaction by polyethylene glycol modification. The effect was increased when polyethylene glycol used in the modification had a higher molecular weight. This Example was carried out to examine whether or not the effect was increased by modifying antibody fragments with a polymer in comparison with an unmodified antibody fragment.

[Methods]

F(ab')$_2$ specific to a non-specific reaction factor was chemically modified with polyethylene glycol of 20 kDa having a succinimide group at the terminus of one side to prepare a polyethylene-glycol-modified F(ab')$_2$ [hereinafter referred to as F(ab')$_2$Suc]. Similarly, the thiol-group-blocked Fab' was chemically modified with the same polyethylene glycol to prepare a modified product (hereinafter referred to as Fab'Suc). With respect to the inhibitory effect, F(ab')$_2$Suc, Fab'Suc, and Fab'Mal of the present invention were compared with F(ab')$_2$. In this regard, these antibody fragments or chemically modified antibody fragments used in this Example were prepared from the same lot of antibody.

[Preparation of F(ab')$_2$Suc and Fab'Suc]

A rabbit anti-human IgM polyclonal antibody IgG (homemade) was digested with pepsin to prepare F(ab')$_2$. The thiol-group-blocked Fab' was prepared in accordance with the method described in Example 1. The resulting F(ab')$_2$ and thiol-group-blocked Fab were dialyzed using a 50 mmol/L phosphate buffer (pH 6.0) containing 5 mmol/L EDTA, as an external fluid. To a 5 mg/mL F(ab')$_2$ or thiol-group-blocked Fab solution, polyethylene glycol of 20 kDa having a succinimide group (manufactured by NOF CORPORATION) was added to carry out a reaction at 4° C. for 12 hours while stirring. The resulting reaction liquid was subjected to gel filtration to collect F(ab')$_2$Suc and Fab'Suc fractions of interest, which were concentrated to approximately 5 mg/mL.

[Assay Conditions for Evaluating the Effects of Non-Specific Reaction Inhibitors]

Under the same assay conditions described in Example 1, the antibody fragments modified with polyethylene glycol were compared with unmodified F(ab')$_2$ to examine the effect of inhibiting a non-specific reaction. In this Example, the effect was evaluated using R1 supplemented with each non-specific reaction inhibitor at a final concentration of 0 mg/L, 20 mg/L, 50 mg/L, or 100 mg/L. As samples to be assayed, the same samples A and B as those used in Example 1 were used.

[Results]

Figure 2:
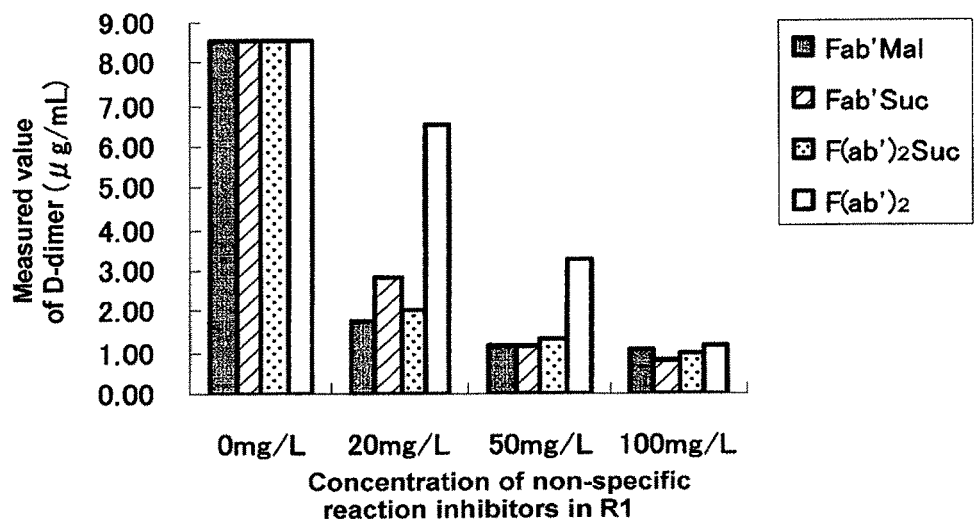
FIG. 2 is a graph showing the effects of inhibiting a non-specific reaction (sample to be assayed=sample A) with respect to F(ab')$_2$Suc, Fab'Suc, and Fab'Mal (non-specific reaction inhibitors of the present invention) which are modified with polyethylene glycol of 20 kDa, as well as unmodified F(ab')$_2$ for comparison.
Figure 3:
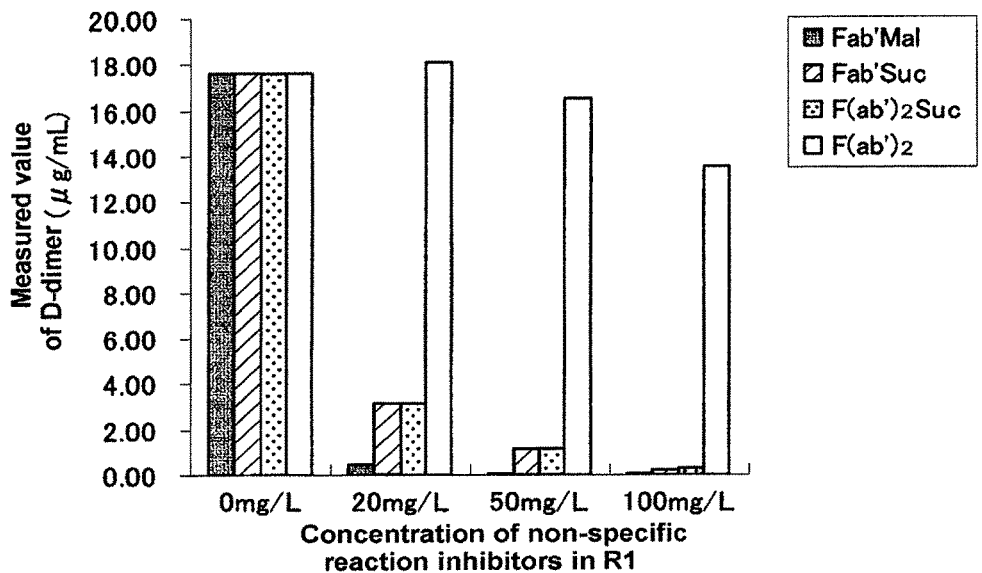
FIG. 3 is a graph showing the effects of inhibiting a non-specific reaction (sample to be assayed=sample B) with respect to F(ab')$_2$Suc, Fab'Suc, and Fab'Mal (non-specific reaction inhibitors of the present invention) which are modified with polyethylene glycol of 20 kDa, as well as unmodified F(ab')$_2$ for comparison.

The results are shown in FIG. 2 (sample A) and FIG. 3 (sample B). As shown in FIG. 2, it was found that F(ab')$_2$Suc, Fab'Suc, and Fab'Mal, which were modified with polyethylene glycol of 20 kDa, exhibited a remarkably increased effect of inhibiting a non-specific reaction, in comparison with unmodified F(ab')$_2$.

Example 3

[Object]

As shown in the results of Example 2, it was found that an antibody fragment modified with polyethylene glycol exhibited a remarkably enhanced effect of inhibiting a non-specific reaction, in comparison with an unmodified antibody fragment. The object of this Example is to clarify the effects of the present invention by comparing the present invention with the addition of IgG as prior art.

[Methods]

With respect to the inhibitory effect, Fab'Mal of 20 kDa, IgG, and F(ab')$_2$ were compared with each other. These three substances were prepared from the same lot of IgG.

[Assay Conditions for Evaluating the Effects of Non-Specific Reaction Inhibitors]

Under the same assay conditions described in Example 1, the effect of inhibiting a non-specific reaction was examined. In this Example 3, R1 supplemented with each of IgG, F(ab')$_2$, or Fab'Mal of 20 kDa at a concentration of 50 mg/L was used for the examination.

[Results]

Figure 4:
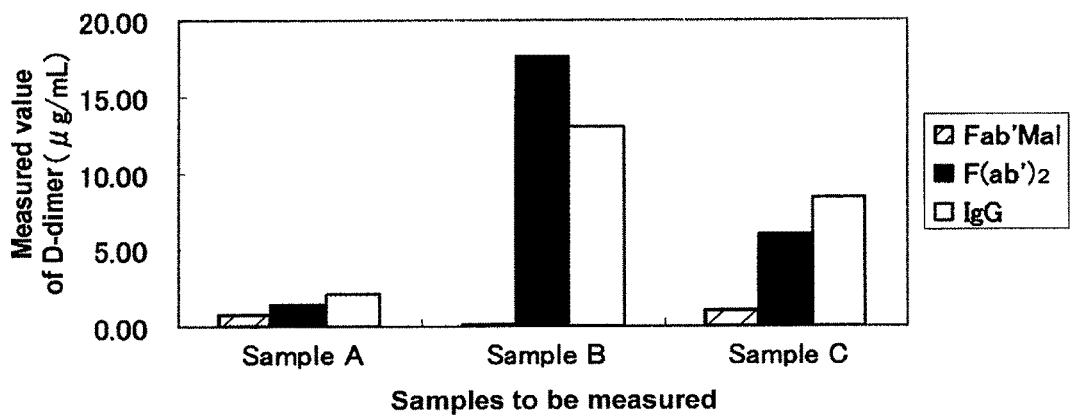
FIG. 4 is a graph showing the effects of inhibiting a non-specific reaction with respect to Fab'Mal (non-specific reaction inhibitor of the present invention) which is modified with polyethylene glycol of 20 kDa, as well as unmodified IgG and F(ab')$_2$ for comparison.

The result is shown in FIG. 4. As shown in FIG. 4, it was found that Fab'Mal modified with the polymer exhibited a remarkably increased effect of inhibiting a non-specific reaction, in comparison with IgG and F(ab')$_2$. This result shows that the present invention is superior to at least unmodified IgG as prior art in the effect of inhibiting a non-specific reaction.

Example 4

[Object]

It was found that an embodiment of the non-specific reaction inhibitor, Fab'Mal, was highly effective in inhibiting a non-specific reaction in comparison with IgG and F(ab')$_2$. The following Example was carried out to examine an immunological nephelometric reaction which was a problem in prior art.

[Methods]

Figure 5:
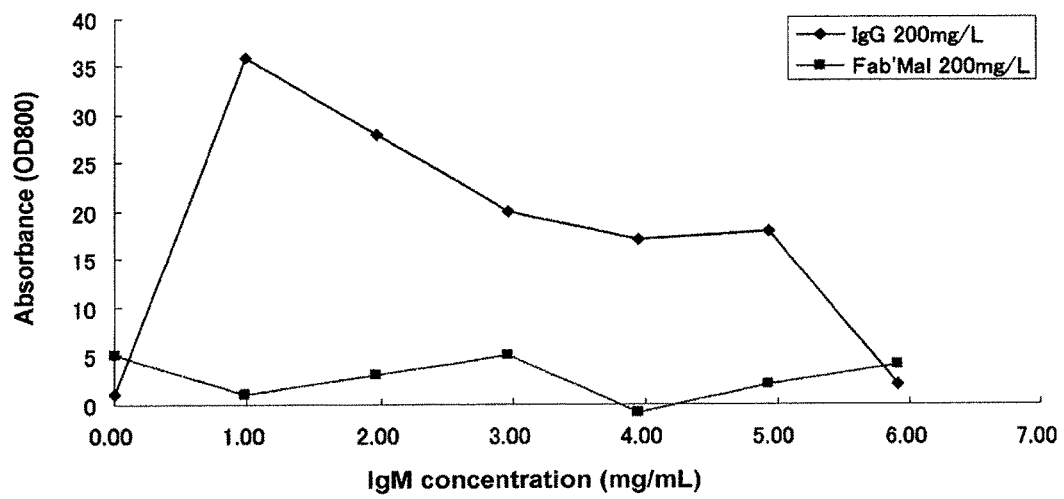
FIG. 5 is a graph showing immunological nephelometric reactions detected by changes in absorbance, with respect to Fab'Mal (non-specific reaction inhibitor of the present invention) which is modified with polyethylene glycol of 20 kDa, as well as unmodified IgG for comparison.

An immunological nephelometric reaction tends to appear when an antigen and an antibody specific thereto coexist at high concentrations. In this Example, a human IgM (homemade) was used as an antigen, and Fab'Mal of 20 kDa was used as a substance corresponding to an antibody. IgG or Fab'Mal was added to R1 of the agent for measuring a D-dimer at a concentration of 200 mg/L. As samples to be measured, samples containing a human IgM at concentrations within a range of 0.99 mg/mL to 5.9 mg/mL were used, as shown in FIG. 5. It is known that an IgM level in healthy persons generally falls within a range of 1.00 mg/mL to 1.5 mg/mL. This Example was carried out within a possible range of an IgM level in the measurement of a human plasma or serum sample. The influence of the immunological nephelometric reaction was optically measured at a wavelength of 800 nm using HITACHI 7170.

[Assay Conditions for Evaluating Immunological Nephelometric Reaction]

Each sample, R1, and R2 were reacted at a ratio of 10 μL:180 μL:180 μL, and an increase in absorbance detected at a wavelength of 800 nm was measured using HITACHI 7170.

[Results]

The result is shown in FIG. 5, which shows changes in absorbance between the mixing of each sample with the R1 liquid and the point immediately before the addition of the R2 liquid. Under the conditions, it can be judged that an immunological nephelometric reaction occurs when an increase in absorbance is observed.

The present inventors confirmed that an increase in absorbance was not observed even when Fab'Mal was used at a high concentration of 800 mg/L.

Example 5

[Object]

It was found from Example 4 that an immunological nephelometric reaction did not easily occur when Fab'Mal was used. In this Example, the stability in storage of the present invention was examined.

A molecule of F(ab')$_2$ degrades into two molecules of Fab'. In particular, when F(ab')$_2$ is added to R1 and stored as a mixture, F(ab')$_2$ easily degrades into Fab', and this phenomenon causes a problem. This is because Fab' exhibits a weak effect of inhibiting a non-specific reaction, and thus, a gradual increase in measured values is observed when a sample which cause a non-specific reaction is measured. In Example 5, the effect of inhibiting a non-specific reaction was examined after the storage at 37° C. to clarify the stability in storage of Fab'Mal. In general, an appropriate storage of a reagent for immunological measurement is carried out at 4° C. When a reagent is stored at 37° C., a decrease in the effect of inhibiting a non-specific reaction can be observed earlier, in comparison with a storage at 4° C. This is because the degradation into Fab' is easily accelerated at 30° C. to 40° C. In addition, at this temperature range, F(ab')$_2$ is subject to major factors for promoting the degradation into Fab', such as a protease-like factor or an oxidation-reduction reaction. In this Example, the stability of Fab'Mal was examined by selecting storage conditions at 37° C., which remarkably promoted the degradation of F(ab')$_2$ and actually caused the deterioration of a reagent.

[Methods]

An R1 reagent supplemented with F(ab')$_2$ or Fab'Mal was prepared to examine the effect of inhibiting a non-specific reaction after the storage of the R1 reagent at 37° C. The inhibitory effect was evaluated by the measurement using sample A.

[Assay Conditions for Evaluating Stability in Storage]

R1 supplemented with 200 mg/L F(ab')$_2$ or Fab'Mal was prepared to examine differences after the storage at 37° C.

In this Example, the R1 reagents were stored at 37° C. for 17 days, and the measurement of sample A was carried out at day 0, day 5, day 10, and day 17. The measurement of sample A was carried out using HITACHI 7170 under the conditions similar to those described in Example 1.

[Results]

Figure 6:
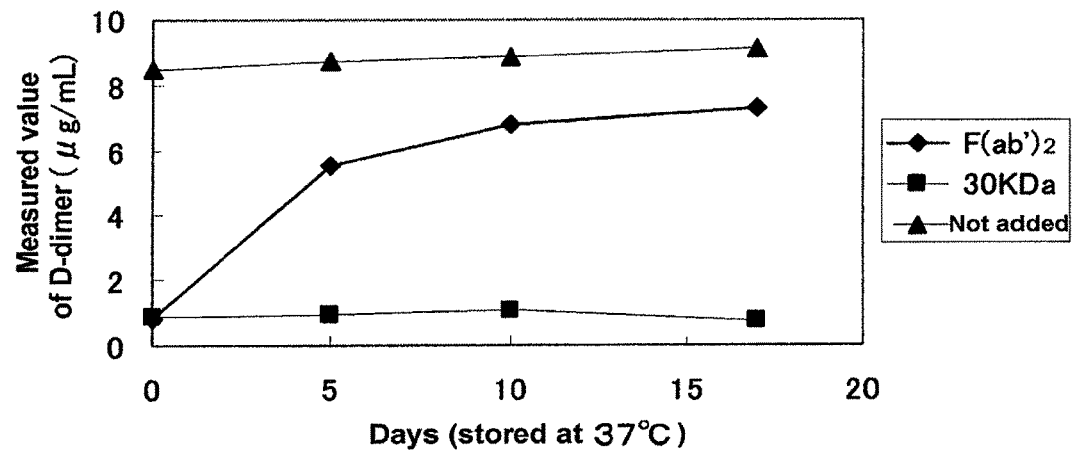
FIG. 6 is a graph showing the stability of storage, with respect to Fab'Mal (non-specific reaction inhibitor of the present invention) which is modified with polyethylene glycol of 20 kDa, as well as unmodified F(ab')$_2$ for comparison.

The result is shown in FIG. 6. As shown in FIG. 6, when F(ab')$_2$ was added to R1 and stored at 37° C., values obtained by measuring sample A were gradually increased. By contrast, with respect to Fab'Mal, an increase in measured values was not observed until day 17. This result clarified that Fab'Mal exhibited a high stability in storage, in comparison with F(ab')$_2$ showing a low stability.

Example 6

[Object]

To examine an embodiment other than Fab'Mal, a complex (hereinafter referred to as Fab'BSA) in which BSA was linked to Fab' via the thiol group contained in the hinge region of the Fab' was prepared to examine the effect of inhibiting a non-specific reaction.

[Methods]

A crosslinking reagent having a maleimide group and a succinimide group, EMCS (manufactured by DOJIN), was reacted with BSA via amino groups located on the surface of BSA. The resulting EMCS-modified BSA was linked to Fab'. The inhibitory effect was measured in a similar fashion described in Example 1, except that R1 supplemented with Fab'BSA at a concentration of 0 mg/L, 33 mg/L, 66 mg/L, or 133 mg/L was used.

[Preparation of Fab'BSA]

To a BSA solution (5 mg/mL) prepared by dissolving BSA (manufactured by SIGMA) in a 50 mmol/L phosphate buffer (pH 6.0) containing 5 mmol/L EDTA, EMCS (DOJIN) was added to become a concentration of 5 mmol/L. A mixture was incubated at 37° C. for 1 hour, and was subjected to gel filtration to collect a BSA fraction. As a running buffer for the gel filtration, a 200 mmol/L Tris buffer (pH 8.2) containing 150 mmol/L NaCl was used. Fab' was prepared from an anti-human IgM antibody in accordance with the method described in Example 1. The EMCS-modified BSA was mixed with 5 mg/mL Fab', and reacted at 4° C. for 16 hours while stirring. The reaction liquid was subjected to gel filtration to collect an Fab'BSA fraction of interest, which was concentrated to approximately 5 mg/mL. As a running buffer for the gel filtration, a 50 mmol/L phosphate buffer (pH 6.0) containing 5 mmol/L EDTA was used.

Figure 7:
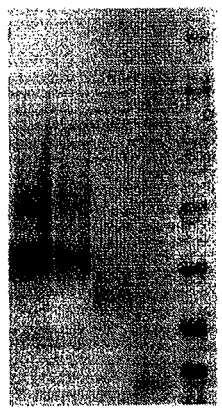
FIG. 7 shows the result of SDS-polyacrylamide gel electrophoresis (SDS-PAGE) of Fab'BSA prepared in Example 6.

The result of SDS-polyacrylamide gel electrophoresis (SDS-PAGE) of the resulting Fab'BSA is shown in FIG. 7. In FIG. 7, Fab'BSA, Fab'BSA, F(ab')$_2$, Fab', and markers are shown (from the left lane).

[Results]

As shown in Table 2, an embodiment of the present invention, Fab'BSA, exhibited the effect of inhibiting a non-specific reaction in a concentration-dependent manner. It was clarified from this result that the inhibitory effect was not specific to polyethylene glycol, and that the same effect was obtained when BSA was linked to Fab'.

TABLE 2

| Fab'BSA | 0 mg/L | 33 mg/L | 66 mg/L | 133 mg/L |
|---|---|---|---|---|
| Sample A | 10.26 | 4.96 | 2.16 | 1.01 |

Example 7

[Object]

To examine an embodiment other than Fab'Mal and Fab'BSA, a complex (hereinafter referred to as Fab'PG) in which polyglutamic acid was linked to Fab' via the thiol group contained in the hinge region of the Fab' was prepared to examine the effect of inhibiting a non-specific reaction.

[Methods]

A crosslinking reagent having a maleimide group and a succinimide group, EMCS (manufactured by DOJIN), was reacted with polyglutamic acid via the amino group of the amino-terminus of polyglutamic acid. The resulting EMCS-modified polyglutamic acid was linked to Fab'. The inhibitory effect was measured in a similar fashion described in Example 1, except that R1 supplemented with Fab'PG at a concentration of 0 mg/L, 5 mg/L, 50 mg/L, or 100 mg/L was used.

[Preparation of Fab'PG]

To a 5 mg/mL polyglutamic acid solution prepared by dissolving polyglutamic acid (manufactured by and purchased from SIGMA) having a molecular weight of 15 kDa to 50 kDa in a 50 mmol/L phosphate buffer (pH 6.0) containing 5 mmol/L EDTA, EMCS (Dojin) was added to become a concentration of 5 mmol/L. A mixture was incubated at 37° C. for 1 hour, and was subjected to gel filtration to collect a polyglutamic acid fraction. As a running buffer for the gel filtration, a 200 mmol/L Tris buffer (pH 8.2) containing 150 mmol/L NaCl was used. Fab' was prepared from an anti-human IgM antibody in accordance with the method described in Example 1, and was adjusted to a concentration of 5 mg/mL using a 50 mmol/L phosphate buffer (pH6.0) containing 5 mmol/L EDTA. The EMCS-modified polyglutamic acid was mixed with Fab', and reacted at 4° C. for 16 hours while stirring. The reaction liquid was subjected to gel filtration to collect an Fab'PG fraction of interest, which was concentrated to approximately 5 mg/mL. As a running buffer for the gel filtration, a 50 mmol/L phosphate buffer (pH 6.0) containing 5 mmol/L EDTA was used.

[Results]

The result is shown in Table 3. As shown in Table 3, an embodiment of the present invention, Fab'PG, exhibited the effect of inhibiting a non-specific reaction in a concentration-dependent manner. It was clarified from this result that the acquired inhibitory effect was not specific to polyethylene glycol and BSA, and that the same effect was obtained when polyglutamic acid was linked to Fab'.

TABLE 3

|  | 0 mg/L | 25 mg/L | 50 mg/L | 100 mg/L |
| --- | --- | --- | --- | --- |
| Sample D | 16.05 | 7.74 | 1.91 | 1.01 |
| Sample B | 19.14 | 7.79 | 6.62 | 3.83 |

Example 8

[Object]

To examine an embodiment other than Fab'Mal, Fab'BSA, and Fab'PG, a complex (hereinafter referred to as Fab'DX) in which a polysaccharide, dextran, was linked to Fab' via amino groups of the Fab' was prepared to examine the effect of inhibiting a non-specific reaction.

[Methods]

A commercially available activated dextran in which some of the functional groups were converted to aldehyde groups was used, and each aldehyde group was linked to the amino group of the thiol-group-blocked Fab' to prepare Fab'DX. The inhibitory effect was measured in a similar fashion described in Example 1, except that R1 supplemented with Fab'DX at a concentration of 0 mg/L, 27 mg/L, 53 mg/L, 80 mg/L, 101 mg/L, 133 mg/L, or 195 mg/L was used.

[Preparation of Fab'DX]

A coupling kit (manufactured by Pierce) containing activated dextran having a molecular weight of 40 kDa was purchased, and a coupling with Fab' was carried out in accordance with a recommended protocol. The thiol-group-blocked Fab' was prepared in accordance with the method described in Example 1. After 10 mg of activated dextran (dissolved in a phosphate buffer at a concentration of 5 mg/mL), 5 mg of the thiol-group-blocked Fab'(dissolved in a phosphate buffer at a concentration of 5 mg/mL), and 0.4 mL of a cyanoborohydride solution were mixed and reacted at 37° C. for 24 hours while stirring, a 1 mol/L Tris buffer (pH 7.2) was added to the mixture at a final Tris concentration of 200 mmol/L and further reacted at 37° C. for 1 hour. The resulting reaction liquid was subjected to gel filtration to collect an Fab'DX fraction of interest, which was concentrated to approximately 5 mg/mL. As a running buffer for the gel filtration, a 50 mmol/L phosphate buffer (pH 6.0) containing 5 mmol/L EDTA was used.

[Results]

The result is shown in Table 4. The unit of measured values of D-dimer shown in Table 4 is µg/mL. As shown, in Table 4, an embodiment of the present invention, Fab'DX, exhibited the effect of inhibiting a non-specific reaction in a concentration-dependent manner. It was clarified from this result that the acquired inhibitory effect was not specific to polyethylene glycol, BSA, and polyglutamic acid, and that the same effect was obtained when dextran was linked to Fab'. With respect to a linkage method, it was confirmed that the inhibitory effect was obtained by linking a polymer to an amino group of Fab' as a target.

TABLE 4

|  | 0 mg/L | 27 mg/L | 53 mg/L | 80 mg/L |
| --- | --- | --- | --- | --- |
| Sample D | 15.46 | 11.11 | 7.26 | 5.17 |
| Sample B | 19.09 | 14.49 | 15.81 | 16.27 |
|  | 101 mg/L | 133 mg/L | 195 mg/L | |
| Sample D | 3.80 | 2.87 | 1.99 | |
| Sample B | 16.43 | 16.51 | 16.22 | |

Example 9

[Object]

Examples 1 to 8 were carried out with respect to a non-specific reaction caused by IgM. In this Example, the effect of the present invention on a non-specific reaction caused by IgA was examined. As a non-specific reaction inhibitor, an antibody fragment complex [hereinafter referred to as Fab' (L)Mal] in which Fab' prepared from an antibody having an affinity to a human L chain was modified with polyethylene glycol was used. The L chain of human immunoglobulins is commonly included as a constitutive domain in IgG, IgM, IgA, and IgE, and thus, an antibody capable of binding with the human L chain can bind with any type of immunoglobulins including IgG, IgM, IgA, and IgE. Therefore, it is expected that an anti-human L chain antibody can inhibit any non-specific reaction caused by IgM, IgG, IgA, or the like. The object of this Example was to show embodiments using an antibody other than an anti-IgM antibody, and to confirm that the inhibitory effect of a modified fragment of the antibody was increased by modifying the antibody fragment with polyethylene glycol.

[Methods]

Fab'(L)Mal was prepared from Fab' of an anti-human L chain antibody, in a fashion similar to the method of preparing Fab'Mal described in Example 1. The inhibitory effect of Fab'(L)Mal on an IgA-type non-specific sample was examined by comparing it with the effect of an antibody fragment F(ab')$_2$ used in preparing Fab'(L)Mal. A reagent for D-dimer was used as a measurement reagent, and the effects of a non-specific reaction were compared with each other by adding each antibody protein at a concentration of 50 mg/L to R1 contained in the agent. As a sample to be measured, sample E in which a non-specific reaction caused by IgA occurred was used.

[Results]

The result is shown in Table 5. The unit of measured values of D-dimer shown in Table 5 is µg/mL. With respect to sample E, an embodiment of the present invention, Fab'(L)Mal, exhibited the effect of inhibiting a non-specific reaction. It was found that Fab'(L)Mal exhibited a remarkably high inhibitory effect, in comparison with the same protein amount of F(ab')₂. It was found in this Example that even this embodiment of the present invention prepared from an antibody other than an anti-IgM antibody was effective in inhibiting a non-specific reaction. It was confirmed that this embodiment exhibited an inhibitory effect higher than that of prior art. The true value of D-dimer contained in sample E was determined by bringing the sample into contact with the anti-IgA antibody to remove the antibody factor of a non-specific reaction from the sample, and then measuring the d-dimer value.

TABLE 5

|  | Inhibitor not added | F(ab')₂ 50 mg/L | Fab'(L)Mal 50 mg/L | True value |
|---|---|---|---|---|
| Sample E | 49.49 | 12.96 | 1.88 | 1.90 |

INDUSTRIAL APPLICABILITY

The non-specific reaction inhibitor of the present invention may be applied to a use in an immunological measurement.

Although the present invention has been described with reference to specific embodiments, various changes and modifications obvious to those skilled in the art are possible without departing from the scope of the appended claims.

The invention claimed is:

1. A method for inhibiting a non-specific reaction in an immunological measurement, said method comprising:
preparing a sample containing an antigen to be measured;
preparing a solution containing a polymer-modified fragment of an antibody specific to a non-specific reaction factor, wherein the polymer is selected from the group consisting of polyethylene glycol, dextran, bovine serum albumin, and polyglutamic acid, the fragment of the antibody is Fab', and the non-specific reaction factor is selected from the group consisting of IgM, IgG, IgA, IgE, and IgD;
mixing the solution with the sample to react the polymer-modified fragment with the non-specific reaction factor, before an antibody specific to the antigen is reacted with the antigen, and adding the antibody specific to the antigen to the mixture; and
inhibiting a non-specific reaction caused by the non-specific reaction factor.

2. The method according to claim 1, wherein the molecular weight of the polymer is 200 Da to 1000 kDa.

3. The method according to claim 1, wherein the polymer-modified antibody fragment is modified by a chemical modification utilizing a thiol, amino, hydroxyl, or carboxyl group, or a biotin-avidin binding.

4. The method according to claim 1, wherein the immunological measurement is a latex agglutination optical measurement method, an enzyme immunoassay, a nephelometric immunoassay, an enzyme-linked immunosorbent assay, a fluoroimmunoassay, or a radioimmunoassay.

5. A method for inhibiting a non-specific reaction in an immunological measurement, said method comprising:
preparing a sample containing an antigen to be measured;
preparing a solution containing an antibody specific to the antigen and a polymer-modified fragment of an antibody specific to a non-specific reaction factor, wherein the polymer is selected from the group consisting of polyethylene glycol, dextran, bovine serum albumin, and polyglutamic acid, the fragment of the antibody is Fab', and, the non-specific reaction factor is selected from the group consisting of IgM, IgG, IgA, IgE, and IgD;
mixing the solution with the sample to react the non-specific reaction factor with the polymer-modified fragment; and
inhibiting a non-specific reaction caused by the non-specific reaction factor.

6. The method according to claim 5, wherein the molecular weight of the polymer is 200 Da to 1000 kDa.

7. The method according to claim 5, wherein the polymer-modified antibody fragment is modified by a chemical modification utilizing a thiol, amino, hydroxyl, or carboxyl group, or a biotin-avidin binding.

8. The method according to claim 5, wherein the immunological measurement is a latex agglutination optical measurement method, an enzyme immunoassay, a nephelometric immunoassay, an enzyme-linked immunosorbent assay, a fluoroimmunoassay, or a radioimmunoassay.

* * * * *